United States Patent
Huang

(10) Patent No.: US 9,921,202 B2
(45) Date of Patent: Mar. 20, 2018

(54) INTEGRATED EXPERIMENTAL SYSTEM OF HYDROFRACTURING, WATER JET SLOTTING, SEEPAGE AND GAS DISPLACEMENT UNDER TRUE TRIAXIAL STRESS

(71) Applicant: China University of Mining and Technology, Xuzhou-Jiangsu (CN)

(72) Inventor: Bingxiang Huang, Xuzhou (CN)

(73) Assignee: China University of Mining and Technology (CN)

( * ) Notice: Subject to any disclaimer, the term of this patent is extended or adjusted under 35 U.S.C. 154(b) by 35 days.

(21) Appl. No.: 15/110,039

(22) PCT Filed: Apr. 20, 2015

(86) PCT No.: PCT/CN2015/076982
§ 371 (c)(1),
(2) Date: Jul. 6, 2016

(87) PCT Pub. No.: WO2016/141621
PCT Pub. Date: Sep. 15, 2016

(65) Prior Publication Data
US 2017/0003263 A1 Jan. 5, 2017

(30) Foreign Application Priority Data
Mar. 9, 2015 (CN) .......................... 2015 1 0100605

(51) Int. Cl.
*G01N 33/24* (2006.01)
*G01B 21/32* (2006.01)
*G01L 15/00* (2006.01)

(52) U.S. Cl.
CPC ............. *G01N 33/24* (2013.01); *G01B 21/32* (2013.01); *G01L 15/00* (2013.01)

(58) Field of Classification Search
CPC .......... G01N 33/24; G01B 21/32; G01L 15/00
See application file for complete search history.

(56) References Cited

U.S. PATENT DOCUMENTS

| 4,502,338 A * | 3/1985 | Smith | ...................... G01N 3/08 |
| | | | 73/819 |
| 2015/0267370 A1* | 9/2015 | Gupta | ..................... E02D 1/025 |
| | | | 73/818 |

FOREIGN PATENT DOCUMENTS

| CN | 102607950 | 7/2012 |
| CN | 102621000 | 8/2012 |

(Continued)

OTHER PUBLICATIONS

Wawersik et al., New Method for True-Triaxial Rock Testing, 1997, Int. J. Rock Mech. & Min. Sci. 34:3-4, paper No. 330, pp. 1-14.*

*Primary Examiner* — Hezron E Williams
*Assistant Examiner* — David Z Huang
(74) *Attorney, Agent, or Firm* — Dickinson Wright PLLC

(57) ABSTRACT

An integrated experimental system of hydrofracturing, water jet slotting, seepage and gas displacement under true triaxial stress, including: a true triaxial stress loading experimental frame, a loading system and a monitoring system. The true triaxial stress loading experimental frame and the loading system are connected by oil pipes; the monitoring system is connected to the true triaxial stress loading experimental frame and the loading system by signal lines; the true triaxial stress loading experimental frame comprises a main experimental bench and six flat jacks; a loading cavity for test block is equipped in the main experimental bench; the six flat jacks are set in the loading cavity; and a space of regular hexahedron is formed by the six flat jacks.

9 Claims, 8 Drawing Sheets

(56) References Cited

FOREIGN PATENT DOCUMENTS

| | | |
|---|---|---|
| CN | 102735547 | 10/2012 |
| CN | 102735548 | 10/2012 |
| CN | 102735549 | 10/2012 |
| CN | 103883301 | 6/2014 |
| KR | 20050020057 | 3/2005 |

\* cited by examiner

INTEGRATED EXPERIMENTAL SYSTEM OF HYDROFRACTURING, WATER JET SLOTTING, SEEPAGE AND GAS DISPLACEMENT UNDER TRUE TRIAXIAL STRESS

CROSS-REFERENCE TO RELATED APPLICATIONS

The present application is a 35 U.S.C. Section 371 national stage filing of International Patent Application No. PCT/CN2015/076982, filed 20 Apr. 2015, and through which priority is claimed to Chinese Patent Application CN 201510100605.2, filed on 9 Mar. 2015, the disclosures of which are incorporated herein by reference in their entireties.

TECHNICAL FIELD

The present invention relates to the technical field of coal mining, in particular, to an integrated experimental system of hydrofracturing, water jet slotting, seepage and gas displacement under true triaxial stress.

BACKGROUND ART

The control of hard roof, the prevention and treatment of coal and rock burst, the gas extraction in coal seams with low permeability, the prevention and treatment of coal and gas outburst, and fully-mechanized top coal caving in hard and thick or extremely thick coal seams are technical problems faced in underground coal mining. Transforming the structure of coal and rock masses is the core issue in solving all of these problems, by increasing the number of hydraulic fractures in the coal and rock strata, their strength can be weakened and permeability can be improved. At present, hydraulic fracturing is an effective method to realize the structure transformation of coal and rock masses.

The existence of the complex structure of coal and rock strata, soft coal seam, adsorption and desorption effect of methane, developed natural fractures, anisotropy of coal seam and the influence of mining work result in the hydraulic fracturing of coal-rock mass becoming complicated, which has been proved by underground coal mine hydraulic fracturing and coal-bed-methane exploitation.

The propagation of hydraulic fractures and their morphology are complex in hydraulic fracturing. Real-time propagation and morphology of hydraulic fractures cannot be monitored precisely at present. The propagation law of hydraulic fractures in site is not revealed, which result in the blindness and poor effect of hydraulic fracturing. The development and popularization of hydraulic fracturing technology are restricted. Meanwhile, there is no a complete set of experimental system in coal industry to study these problems systematically and thoroughly. It is urgent to develop a complete set of experimental system to study the mechanism of the above problems.

DISCLOSURE OF THE INVENTION

To solve the above problems, the present invention provides an integrated experimental system of hydrofracturing, water jet slotting, seepage and gas displacement under true triaxial stress.

In an embodiment, the integrated experiment system of hydrofracturing, water jet slotting, seepage and gas displacement under true triaxial stress includes a true triaxial stress loading experimental frame, a loading system and a monitoring system;

The true triaxial stress loading experimental frame and the loading system are connected by oil pipes;

The monitoring system is connected to the true triaxial stress loading experimental frame and the loading system by signal lines separately;

The true triaxial stress loading experimental frame consists of a main frame and six flat jacks;

A loading cavity of test block is arranged in the main frame;

The six flat jacks are positioned in the loading cavity;

A space of regular hexahedron is formed by the six flat jacks.

Furthermore, the true triaxial stress loading experimental frame includes a baseplate, an upper cover plate, displacement restricting steel columns, a caging device, an annulus steel ring and arc-shaped subplates;

The upper cover plate and the baseplate are positioned at the two ends of the annulus steel ring;

The upper cover plate and the baseplate are fitted together by displacement restricting steel columns;

Four arc-shaped subplates are arranged uniformly in the annulus steel ring;

The four arc-shaped subplates contact with the four side surfaces of the regular hexahedron.

Furthermore, the loading system includes a six-channel hydraulic-pressure stabilizer controlled loading system and a four-channel electro-hydraulic servo controlled loading system;

The six-channel hydraulic-pressure stabilizer controlled loading system and the four-channel electro-hydraulic servo controlled loading system are connected with the true triaxial stress loading experimental frame by oil pipes;

The four-channel electro-hydraulic servo controlled loading system is connected to the true triaxial stress loading experimental frame by a four-channel oil-water transition supercharger;

The six-channel hydraulic pressure stabilizer controlled loading system is connected to the true triaxial stress loading experimental frame by a flow divider.

Furthermore, the flow divider includes three oil pipes on the inlet side and six oil pipes on the outlet side;

Each oil inlet pipe is connected with two oil outlet pipes;

The flow divider is positioned in the flow divider casing;

Three oil inlet holes are drilled through one side of the flow divider casing, and six oil outlet holes are drilled through the other side of the flow divider casing;

The flow divider includes an upper cover;

The flow divider includes an oil drain valve at the bottom.

Furthermore, the monitoring system includes a data processor, pressure sensors and a deformation monitoring system;

The pressure sensors and deformation monitoring system are connected with the data processor by signal lines;

Three pressure sensors are mounted on the flow divider;

The deformation monitoring system includes twenty four displacement sensors;

The displacement sensors are installed in the arc-shaped subplates of the flat jacks inconspicuously;

The lines of displacement sensors are placed in grooves on the side surface of the arc-shaped subplates and gathered to its upper surface;

The displacement sensors are connected with data lines by quick connectors, of which the female connectors are installed on the upper surface of the arc-shaped subplates.

Furthermore, the integrated experimental system of hydrofracturing, water jet slotting, seepage and gas displacement under true triaxial stress includes a hydrofracturing system under true triaxial stress, wherein:

The hydrofracturing system under true triaxial stress includes a similar material casting simulation system with naked borehole, a rock borehole sealing system, bending borehole packers and a multi-borehole simultaneously and independently controlled fracturing system;

The similar simulation material casting system, the rock borehole sealing system, the bending borehole packer and the multi-borehole simultaneously and independently controlled fracturing system are set in parallel;

The similar simulation material casting system includes a thin round bar and a string wrapped on one end of the bar;

The rock borehole sealing system includes O-ring and sealant;

The bending borehole packer includes the vertical section without fracturing hole and inclined section with fracturing holes, to simulate hydraulic fracturing under heterotropic stress field;

The fracturing system controlled by independent multiple boreholes includes a set of molds with cover plate of multi-borehole and caging device, and fluid pressure fracturing controlled by as many as five independent boreholes can be conducted;

Furthermore, the integrated experimental system of hydrofracturing, water jet slotting, seepage and gas displacement under true triaxial stress includes seepage and gas displacement system under true triaxial stress;

The seepage and gas displacement system under true triaxial stress includes an upper seepage plate and a bottom seepage plate;

Seepage orifices are arrayed on the upper and bottom seepage plates;

The upper seepage plate includes a water inlet and a fracturing orifice;

The bottom seepage plate includes a water outlet;

The interstice between the seepage and gas displacement system under true triaxial stress and the test block is filled by sealant;

Furthermore, the integrated experimental system of hydrofracturing, water jet slotting, seepage and gas displacement under true triaxial stress includes a water jet slotting experimental system;

The water jet slotting system is connected with the true triaxial stress loading experimental frame to conduct water jet slotting experiment.

Furthermore, the water jet slotting system includes an electromechanical control cabinet, a high pressure pump control cabinet and a water jet slotting device;

The water jet slotting device consists of a rotary motor, a traction motor, a base plate, two guide rails, a drill pipe, two axial bearings, a propulsion thread rod, a high pressure rotating joint, two sliding blocks and a support frame;

The guide rails are fixed on the support frame;

The baseplate is connected with the guide rails by two sliding blocks;

The drill pipe is fixed on the base plate by axial bearings;

Belt pulleys are fitted on the end of the rotary motor and the drill pipe;

The drill pipe is driven to rotate clockwise or anticlockwise by the rotating motor through belt pulleys;

The traction motor is fixed on the guide rails;

The propulsion thread rod is fixed on the guide rails by two axial bearings;

Threads exist on the surface of the propulsion thread rod;

A belt pulley is fitted on one end of the propulsion thread rod, and is connected with the belt pulley on the motor by a belt.

Using the present invention, the seepage and fluid-structure interaction experiments with high seepage pressure under true triaxial stress can be conducted, the mechanical deformation tests of coal and soft rock under true triaxial stress can be achieved, and experiments of borehole drilling, high pressure water jet slotting can also be realized. The present invention has the integrated functions of hydrofracturing, water jet slotting, seepage and gas displacement under true triaxial stress. These functions can be used in any combination according to specific experiment requirements. The hydraulic fracturing process can be studied and judged systematically and precisely by this invention, and the construction effect and safety are improved significantly.

APPENDED DRAWING REFERENCE SIGNS

Figures 1, 2, 3:
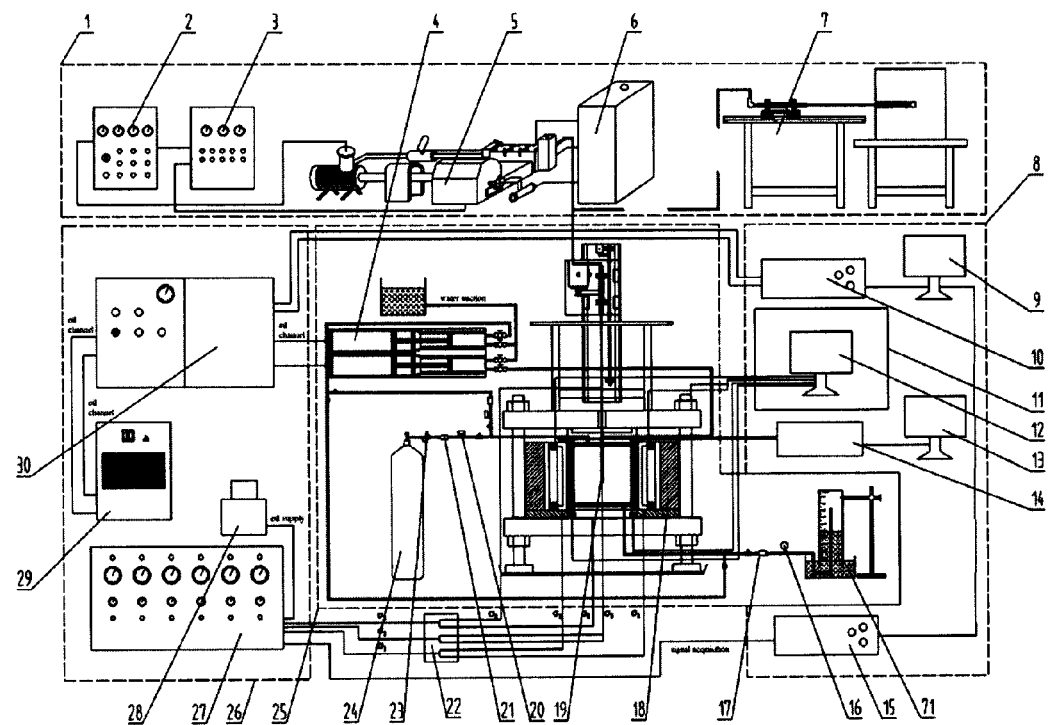
FIG. 1 shows a schematic diagram of an integrated experimental system of hydrofracturing, water jet slotting, seepage and gas displacement under true triaxial stress.
FIG. 2 shows a schematic diagram of a true triaxial stress loading experimental frame according to an embodiment of the present invention.
FIG. 3 shows the overhead view of FIG. 2.
Figure 4:
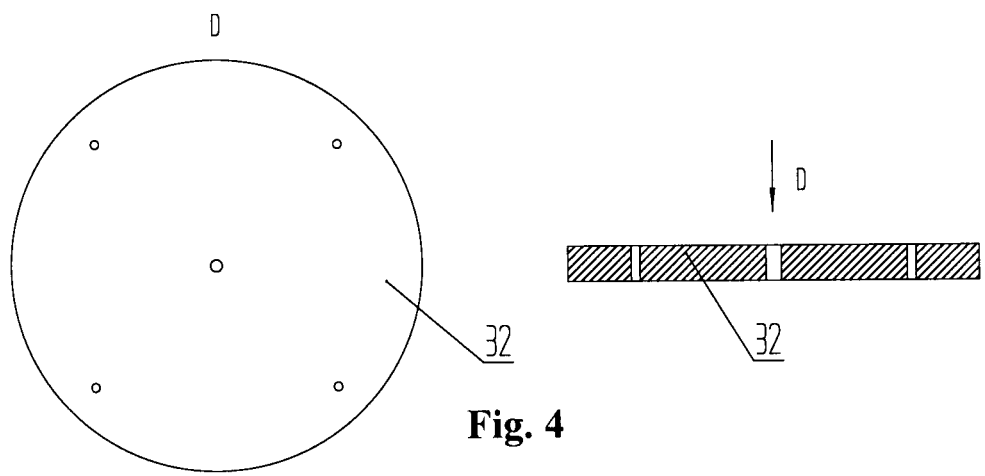
FIG. 4 shows a schematic diagram of an upper cover plate according to an embodiment of the present invention.

1 water jet slotting system, 2 electromechanical control cabinet, 3 high-pressure pump control cabinet, 4 four-channel oil-water transition supercharger, 5 high-pressure pump, 6 water tank, 7 water jet slotting experimental bench, 8 monitoring system, 9 monitoring computer, 10 servo controller, 11 deformation monitoring system, 12 deformation monitoring computer, 13 acoustic emission (AE), 14 AE instrument, 15 hydraulic controller, 16 concentration sensor, 17 first flow sensor, 18 true triaxial stress loading experimental frame, 19 naked borehole fracturing section, 20 pressure sensor, 21 second flow sensor, 22 flow divider, 23 pressure regulating valve, 24 gas storage tank, 25 integrated true triaxial stress loading experimental system, 26 loading system, 27 six-channel hydraulic-pressure stabilizer, 28 oil pump, 29 cooling air conditioning, 30 four-channel servo loader, 31 loading cavity, 32 upper cover plate, 33 upper flat jack, 34 pre-tightening nut, 35 displacement restricting steel column, 36 annulus steel ring, 37 bottom subplate, 38 bottom flat jack, 39 baseplate, 40 side flat jack, 41 arc-shaped subplate, 42 caging device, 43 chamfer, 44 lifting hole, 45 oil pipe, 46 oil pipe groove, 47 oil inlet pipe, 48 oil outlet pipe, 49 cover, 50 flow divider casing, 51 oil drain valve, 52 displacement sensor, 53 quick connector, 54 wire groove, 55 string, 56 thin round bar, 57 borehole packer, 58 test block, 59 O-ring, 60 sealant, 61 sealing section, 62 thread section, 63 fracturing hole, 64 upper seepage plate, 65 water inlet, 66 fracturing orifice, 67 seepage orifice, 68 coal sample, 69 bottom seepage plate, 70 water outlet, 71 oil measure device.

DETAILED DESCRIPTION OF EMBODIMENT

One exemplary embodiment of the invention is hereinafter described in detail with reference to the accompanying drawings. The exemplary embodiment is provided for the purpose of clear understanding and implementation of the invention by those of ordinary skill in the art. It should be appreciated that the accompanying drawings and the exemplary embodiment of the invention is not for use in limiting the invention. The scope of the present invention is defined by the appended claims.

As illustrated in the accompanying drawings, an embodiment of the invention provides an integrated experimental system of hydrofracturing, water jet slotting, seepage and gas displacement under true triaxial stress, including a true triaxial experiment frame 18, a loading system 26 and a monitoring system 8. The true triaxial stress loading experimental frame 18 is connected with the loading system 26 by oil pipes. The monitoring system 26 is connected with the true triaxial stress loading experimental frame 18 and the loading system 26 separately by signal lines. The true triaxial stress loading experimental frame 18 includes a main frame and six flat jacks. The main frame includes a loading cavity 31 inside. The six flat jacks are installed in the loading cavity 31. A regular hexahedron shaped space is formed by the six flat jacks.

Rigid load is applied on the side surfaces of the test block 58 by flat jacks with stroke of 20 mm. On the basis of the stress field, three principal stresses are simulated by three pairs of flat jacks in three orthogonal directions. Four sides of the contact surface of the flat jacks and the test block 58 are made into chamfer 43 with chamfer angle of 45 degrees to ensure that the flat jacks in three orthogonal directions do not squeeze with each other within their effective stroke. The hydraulic pressure of flat jacks is provided by multi-channel pressure stabilizer. The pressure of each channel of the multi-channel pressure stabilizer can be controlled separately.

Furthermore, the true triaxial stress loading experimental frame 18 includes a baseplate 39, an upper cover plate 32, and displacement restricting steel columns 35, a caging device 42, an annulus steel ring 36 and arc-shaped subplates 41. The upper cover plate 32 and the baseplate 39 are installed on two ends of the annulus steel ring 36. The upper cover plate 32 is connected with the baseplate 39 by displacement restricting steel columns 35. The number of the arc-shaped subplates 41 is four. The arc-shaped subplates 41 are arranged uniformly in the annulus steel ring 36. The four arc-shaped subplates 41 contact with the four side surface of the regular hexahedron.

In the true triaxial stress loading experimental frame 18 (FIG. 2 and FIG. 3), the mass of the upper cover plate 32 reaches to 1378.41 kg, and the mass of the upper bearing plate is 76.14 kg. Field sampling of test block 58 with the size of 500 mm×500 mm×500 mm is difficult. To solve this problem, cushion blocks are placed around the six surfaces of test block 58 to simulate the loading of test blocks 58 with different sizes. At present, complete set of cushion blocks with size of 300 mm×300 mm×100 mm have been made, and the mass of single block is 70.2 kg. Simulation of loading on test blocks 58 with the dimension of 300 mm×300 mm×300 mm and 500 mm×500 mm×500 mm can be conducted using this experimental frame.

The diameter of the oil cylinder of the flat jacks is 420 mm, and the load carrying area of the test block 58 is determined by the size of the test block 58. As a result, the hydraulic pressure provided by the control console is not equal to the compress stress exerted on the surface of test block 58. The compress stress exerted on the test block 58 with size of 300 mm×300 mm×300 mm and 500 mm×500 mm×500 mm are determined as 1.5386 and 0.553896 times of the hydraulic pressure provided by control console separately.

The true triaxial stress loading is realized as follows: three principal stresses are exerted by three pairs of flat jacks with strike of 20 mm in three orthogonal directions, and rigid load is applied on the surface of the test block 58 by flat jacks according to the stress field.

The structure of the loading system 26 is as follows. A loading cavity 31 with size of 500 mm×500 mm×500 mm is formed in the loading frame to place the cubic test block 58. Six flat jacks, i.e. an upper flat jack 33, a bottom flat jack 38 and four side flat jacks 40, contact directly with the surfaces of the test block 58. Arc-shaped subplates 41 are installed outside the four side flat jacks 40. The caging device 42 is arranged between two arc-shaped subplates 41. The annulus steel ring 36 is mounted outside the arc-shaped subplates 41. Eight displacement restricting steel columns 35 are installed outside the annulus steel ring 36. The bottom flat jack 38 is embedded into the bottom subplates 37. A baseplate 39 is installed below the bottom subplate 37. An upper cover plate 32 is arranged on the upper flat jack 33. The above is the components of the loading frame 26 and their position relation. The structure of each part and their connection relations are hereinafter described in detail.

Figure 5:
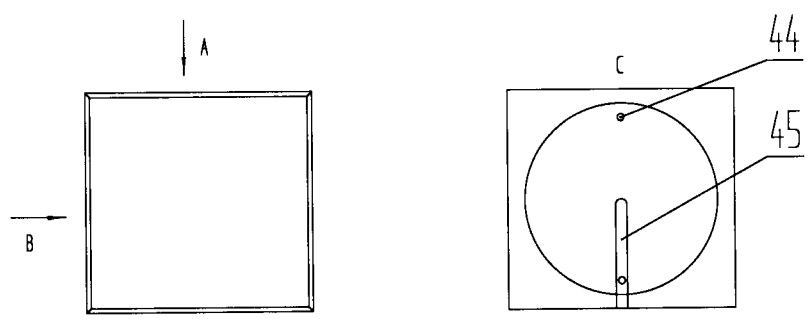
FIG. 5 shows a schematic diagram of a flat jack according to an embodiment of the present invention.
Figure 5:
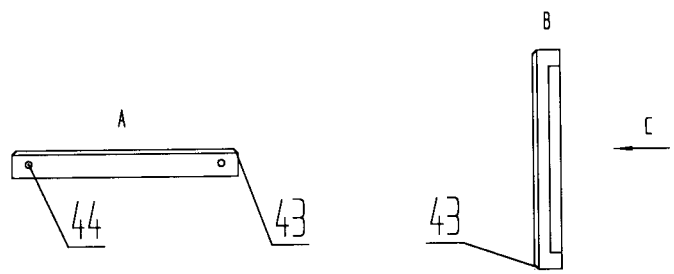
Figure 6:
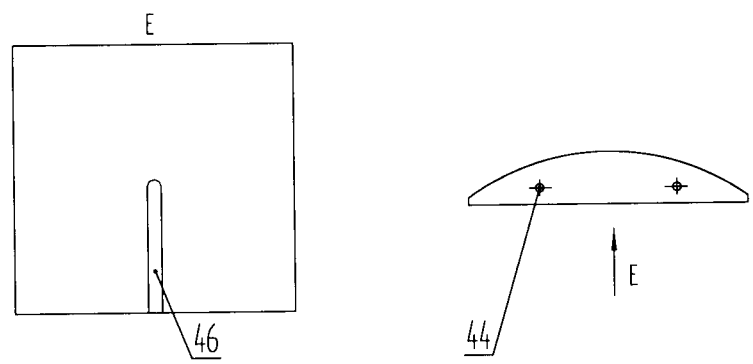
FIG. 6 shows a schematic diagram of an arc-shaped subplate according to an embodiment of the present invention.
Figure 7:
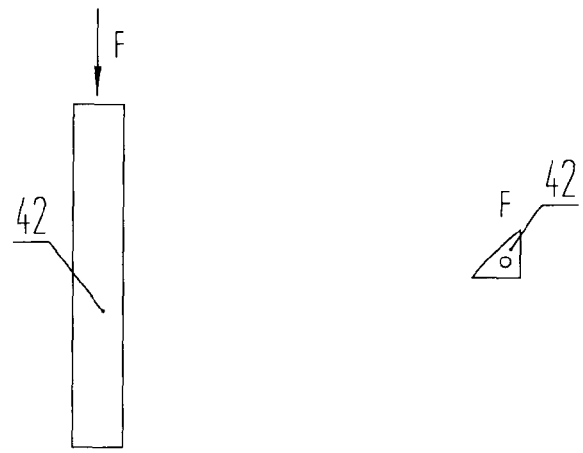
FIG. 7 shows a schematic diagram of a caging device according to an embodiment of the present invention.
Figure 8:
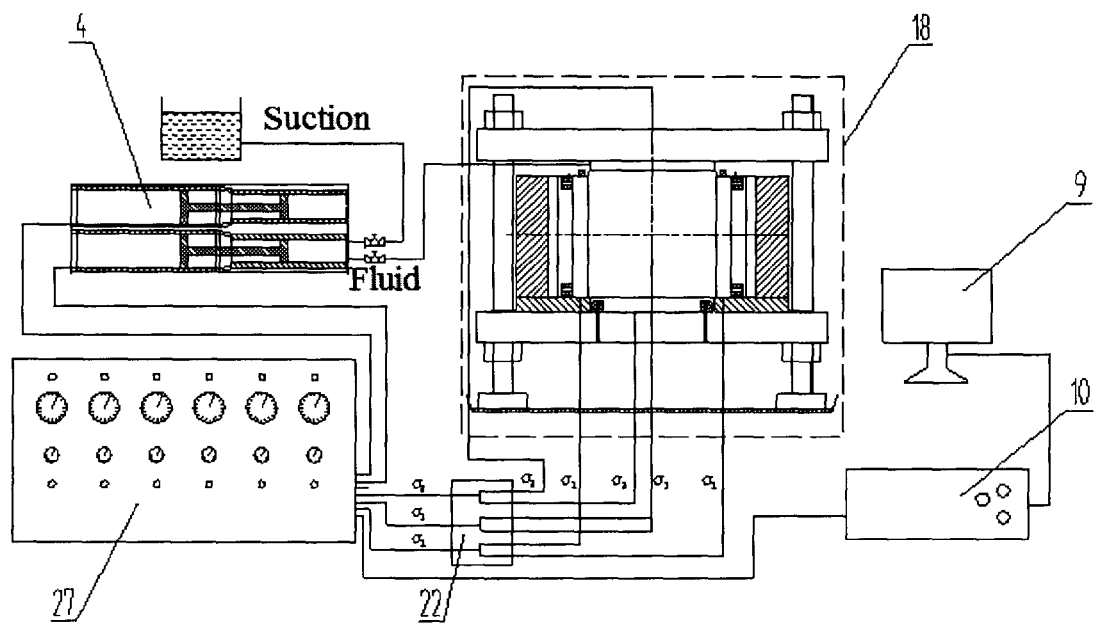
FIG. 8 shows a schematic diagram of six-channel hydraulic pressure stabilizer controlled loading system and four-channel electro-hydraulic servo controlled loading system according to an embodiment of the present invention.

FIG. 5 shows the schematic diagram of the structure of the flat jack. The diameter of the oil cylinder of the flat jack is 420 mm and the effective stroke is 20 mm. Four sides of contact surfaces of the flat jacks and the test block are made into chamfer 43 with chamfer angle of 45 degrees to ensure that the flat jacks in three orthogonal directions do not squeeze with each other within its effective stroke.

The oil pipe 45 is placed in the oil pipe groove 46 of the arc-shaped subplate 41 and passes through the opening in the baseplate 39, and is connected with the flow divider 22.

Each part of the true triaxial stress experimental frame 18 has lifting holes 44.

It is inconvenient to assemble and disassemble the true triaxial stress loading experimental frame 18 because each part of it 18 is very heavy. With lifting hole 44, the installation and uninstallation of the true triaxial stress loading experimental frame 18 can be achieved easily by bridge crane.

At present, the experiments of test block 58 with the size of as large as 500 mm×500 mm×500 mm under true triaxial stress can be realized by the experimental frame 18. At the same time, by placing cushion blocks around the test block 58, the loading of test block 58 with different size can be simulated.

Four sides of the contact surfaces of the cushion blocks and the test block 58 are made into chamfer 43 to eliminate the boundary effect and increase the stroke of the cushion blocks. The flat jacks in three orthogonal directions do not squeeze with each other within its effective stroke and the compress stress is exerted on the test block 58 effectively.

Furthermore, the loading system 26 includes a six-channel hydraulic pressure stabilizer controlled loading system and a four-channel electro-hydraulic servo loading system. The six-channel hydraulic pressure stabilizer controlled loading system and the four-channel electro-hydraulic servo loading system are respectively connected with the true triaxial stress loading experimental frame 18 by oil pipes. The four-channel servo loader 30 and the true triaxial stress loading experimental frame 18 are connected by the four-channel oil-water transition supercharger 4. The six-channel hydraulic pressure stabilizer 27 is connected with the true triaxial stress loading experimental frame 18 by flow divider 22.

The six-channel hydraulic pressure stabilizer controlled loading system and the four-channel electro-hydraulic servo controlled loading system, namely the six-channel hydraulic pressure stabilizer 27 and the four-channel servo loader 30, can work autonomously to conduct single borehole hydraulic fracturing under true triaxial stress. The triaxial stresses loading and the four-channel oil-water transition supercharger 4 can be controlled by any one of the two loading systems. Besides, experiments of multi-borehole hydraulic fracturing and seepage under true triaxial stress can be conducted by cooperation of the two loading systems.

In experiment of single borehole hydraulic fracturing using six-channel hydraulic pressure stabilizer controlled loading system, three channels are used to simulate the triaxial stress, another two channels are used to control two channels of the four-channel oil-water transition supercharger 4 to inject high pressure into the test block 58. The last one channel is reserved.

Triaxial confining pressures can be exerted to simulate the crustal stress by the six-channel hydraulic pressure stabilizer 27, which is controlled by magnetic valves. The pressure stabilizing effect meets the requirements of the experiment system. The water injection is controlled by the loading system with high accuracy. Different loading methods are chosen based on practical needs to realize dynamic control. However, water injection with preset loading method cannot be realized by the six-channel hydraulic pressure stabilizer 27. Besides, the response time of the six-channel hydraulic pressure stabilizer 27 is long and the loading accuracy is low, which do not meet the requirement of the experiment.

In experiments of single borehole hydraulic fracturing using the four-channel electro-hydraulic servo loader 30, three channels of the loading system are used to exert the triaxial confining pressure, and one channel is used to control one channel of the oil-water transition supercharger 4 to inject high water into the test block 58.

To achieve high-accuracy and dynamic control of the water injection system, the four-channel servo loader 30 is used to control the four-channel oil-water transition supercharger 4. Using the four-channel servo loader 30, which is controlled by servo valves, the loading rate of water pressure can be controlled by computer programs and adjusted stepwise in the way of MP/min or mL/min. The loading method can be set arbitrarily to achieve high-accuracy control of fluid (gas) injection system with short response time.

In experiments of single borehole hydraulic fracturing under true triaxial stress, the four-channel servo loader 30 is used to achieve high-accuracy loading of confining pressure and water pressure.

In experiments of multi-borehole hydraulic fracturing or seepage under true triaxial stress, to ensure high-accuracy and independent control of multichannel high-pressure water injection, the four-channel servo loader 30 alone is used to control the four-channel oil-water transition supercharger 4. The triaxial confining pressure is controlled by the six-channel hydraulic pressure stabilizer 27. Special function is achieved by cooperation of the two loading systems.

Cooling air conditioning 29 is used to cool the four-channel servo loader 30.

The electro-hydraulic servo controlled loading system can be extended as conventional mechanical testing machine, i.e., conventional rock mechanics tests can be conducted if the hydraulic pipes are connected to the framework of the mechanical testing machine.

The loading system 26 includes a four-channel servo loader 30; a six-channel hydraulic pressure stabilizer controlled loading system and a high-pressure water experiment bench. Triaxial confining pressure exerted on the test block 58 is loaded by the six-channel hydraulic pressure stabilizer 27 to simulate the in-situ crustal stress. The four channels of the oil-water transition supercharger 4 are controlled independently by the four-channel servo loader 30 to achieve high-accuracy control of the fluid (gas) injection system. Meanwhile, the experimental system has the function of triaxial rock mechanics testing machine, i.e., true triaxial mechanics deformation tests of coal and soft rock can be conducted by the true triaxial experiment system 18.

The confining pressure of the test block 58 is loaded by applying rigid load on the side surface of the test block using flat jacks with stroke of 20 mm. According to the characteristics of the stress field, three principal stresses are simulated by three pairs of flat jacks in three orthogonal directions. Four sides of the contact surface of the flat jack and the test block are made into chamfer 43 with chamfer angle of 45 degrees to ensure that the flat jacks do not squeeze with each other within its effective stroke.

The high-pressure fracturing fluid (gas) of the fluid (gas) injection system is provided by the four-channel oil-water transition supercharger 4. The fracturing fluid (gas) includes water, nitrogen, liquid nitrogen foam and multi-phase fluid like water-sand fracturing fluid. The four channels of the oil-water transition supercharger 4 are controlled separately by the four-channel servo loader 30, and the loading rate of water pressure can be controlled by computer programs and adjusted stepwise in the way of MP/min or mL/min. Thus, high-accuracy control of the fluid (gas) injection system is achieved.

Stable output of pressure by flat jacks is required in the loading of the confining pressure. The loading method can be controlled and the response time and loading accuracy of the loading system 26 meet the requirements of the experimental system.

Based on the above requirements and the working principle of magnetic valves, triaxial confining pressures are loaded on the test block 58 by flat jacks, the oil of which is provided by the six-channel hydraulic pressure stabilizer controlled loading system. The pressure of each channel can be controlled independently, and fluid can be injected at constant flow rate or according to the preset program.

The six-channel hydraulic pressure stabilizer 27 includes an oil pump 28, a pressure stabilizing console based on nitrogen gas, a loading control system, and an automatic data acquisition system. The hydraulic pressure is provided by the electric oil pump 28. The independent loading and unloading of each channel is realized by the nitrogen stabilizer and the hydraulic pressure boosting system, and is controlled and monitored by computer programs. The data of loading pressure, displacement, fluid pressure and flow rate are collected automatically during the experiment. The hydraulic pressure of the oil pump 30 can reach more than 30 MPa, and the flow rate can reach more than 2.5 L/min. The accuracy of the hydraulic pressure stabilizer reaches to 0.5%. The loading path is controlled by computer automatically, and the loading rate of water pressure can be controlled by computer programs in the way of L/min or MP/min. The data of loading pressure, displacement, fluid pressure and flow rate are collected automatically during the experiment. The range of hydraulic pressure is 0 MPa to more than 60 MPa. The range of flow rate is 0~0.5 m$^3$/h. The data acquisition interval is less than one second. The six-channel hydraulic pressure stabilizing system meets the requirements of the true triaxial stress loading system 26.

The crustal stress exerted by the true triaxial stress loading experimental frame 18 is simulated by the six-channel hydraulic pressure stabilizer controlled loading system, the loading of multi-channel water pressure can also be controlled by the loading system in multi-borehole hydraulic fracturing.

The response time and loading accuracy of magnetic valve meets the requirements of the loading of the confining pressure. However, the fluid injection system must be controlled according to different loading paths and methods, and has short response time and high accuracy. The fluid injection system controlled by magnetic valves cannot meet the requirements of the true triaxial fluid fracturing experiment.

Based on the above analysis, servo valves are used to control the loading of the fluid (gas) injection system. Electro-hydraulic servo control system is bought to control the four-channel oil-water transition supercharger 4 independently, in which the high-accuracy control of fluid (gas) injection system is realized. In single borehole hydraulic fracturing, the confining pressure of the true triaxial stress loading experimental frame 18 is controlled by three channels of the four-channel electro-hydraulic servo control system, and the water pressure is loaded by the last channel to realize high-accuracy control of the water pressure. In multi-borehole hydraulic fracturing, the loading of multi-channel water pressure is controlled by the four-channel electro-hydraulic servo control system. The confining pressure can be loaded by the six-channel hydraulic pressure stabilizer 27.

The pressure and flow of fluid in the four-channel oil-water transition supercharger 4 are provided by the four-channel servo controlled loading system. The servo valve is controlled by feedback signals of the pressure and displacement sensors, which are installed at the end of the oil-water transition supercharger 4. Different pressure and flow output can be realized using servo valves. The loading system 26 includes an oil source, a flow divider 22, electro-hydraulic servo valves, a computer acquisition control system and pipe system, and the like.

Each channel of the experimental system has the control functions of the pressure and displacement. The loading and unloading of each channel can be controlled by computer programs and adjusted stepwise in the way of L/min or MPa/min. The loading path can be set as needed and pulse loading with different frequencies can be realized. The loading can be controlled by the displacement monitoring system. The system response frequency is not less than 100 Hz and the response time is less than 10 msec. The electro-hydraulic servo controlled loading system has good reliability with accuracy of 0.5%. The range of data acquisition frequency is large and different acquisition frequencies can be chosen according to specific experiment requirements. The rated flow of the system is 50 L/min and the output flow can be adjusted by a pump with adjustable flow rate to avoid high oil temperature. The flow rate of the four channels are 4 L/min, 4 L/min, 4 L/min and 40 L/min separately. The working pressure of the system can reach 31.5 MPa.

The electro-hydraulic servo controlled loading system can be used together with the six-channel hydraulic pressure stabilizer controlled loading system, the AE 13 and the AE instrument 14. Automatic control and data acquisition can be realized by one computer. The oil pipe system is equipped with position selector valves.

The electro-hydraulic servo controlled loading system can be extended as conventional mechanical testing machine, i.e., conventional rock mechanics tests can be conducted if the hydraulic pipes are connected with the framework of the testing machine.

The transition of oil pressure to fluid (gas) pressure is achieved by the four-channel oil-water transition supercharger 4, which includes four oil cylinders, four water cylinders, four pistons in oil cylinders, four pistons in water cylinders and the connecting rods between oil piston and water piston. The diameter of the oil cylinder is greater than that of the water cylinder, the joint of the oil and water cylinder present "T" shape, O-ring is installed and gas vent is drilled on the T-shaped joint of the oil and water cylinder. Inlet and outlet system is mounted at the end of the water cylinder.

Valves and quick connectors are arranged on the oil inlet pipes 47 and oil outlet pipes 48. The inlet and outlet system includes a water inlet pipe and a water outlet pipe connected with the water tank 6. A one-way valve is installed on the water inlet pipe. A one-way valve, a pressure gage and a quick connector are installed on the water outlet pipe successively.

The reciprocating motion of the oil cylinder piston leads to the reciprocating motion of the water cylinder piston. The suction and drainage of water in the water cylinder and the transform of oil pressure to water pressure are realized by the reciprocating movement of the water cylinder piston and oil cylinder piston. The water pressure is higher than the oil pressure because the diameter of the oil cylinder is greater than that of the water cylinder. The supercharge ratio can be adjusted by adjusting the diameter ratio of the oil cylinder to the water cylinder. In the four-channel oil-water transition supercharger 4, the diameter of oil cylinder is the square root of two times of the diameter of water cylinder. As a consequence, the water pressure is twice of the oil pressure. The water pressure of the water injection system can reach 63 MPa because the oil pressure of the four-channel oil-water transition supercharger 4 which is provided by electro-hydraulic servo control system can reach 31.5 MPa. The O-ring 59 is installed on the junction of the oil and water cylinder to prevent oil entering into the water cylinder. An air exhaust opening is positioned at the water cylinder side, which is used in water suction process to remove air in the water cylinder. The transition of oil pressure to water pressure is realized and a method for high-pressure water injection in coal seam is provided. Meanwhile, rock mechanics tests with water injection are convenient to conduct using this system. The oil-water transition supercharger 4 is easy to use with simple structure, and can be used widely.

Displacement sensors 52 are mounted on each oil cylinder and the displacement of each oil cylinder piston can be monitored during the experiment. Four water (gas) channels are controlled by the oil-water (gas) transition supercharger 4 and 10 L water can be injected by one water cylinder.

Each of the four channels is equipped with displacement sensor 52, which is connected with the piston. In the experiment, the injection volume is controlled by the displacement of the piston.

The diameter of water cylinders in the four-channel oil-water transition supercharger 4 is greater than that of the former water cylinder and more water can be accommodated. Displacement sensors 52 are connected with the four pistons of the four-channel oil-water transition supercharger 4. The water injection volume can be monitored by the displacement of the piston. The water injection rate is controlled by the feedback signals of the displacement sensors 52. The water suction process of the water cylinder is controlled by magnetic valves, by which automatic water suction is achieved.

Figure 10:
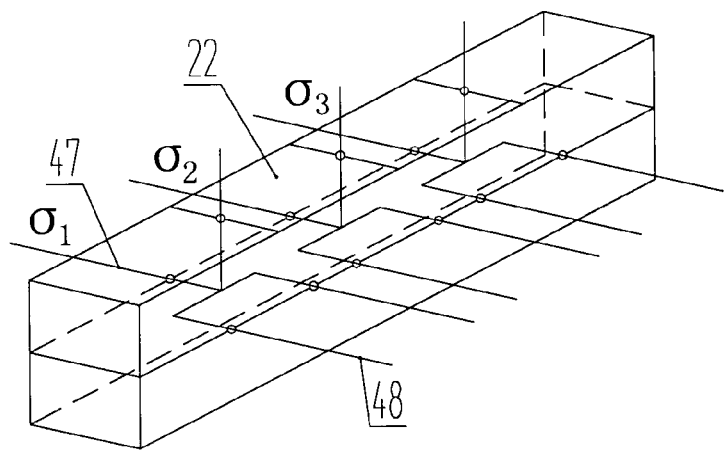
FIG. 10 shows a schematic diagram of flow divider according to an embodiment of the present invention.

The loading of true triaxial confining pressures are conducted by the six-channel hydraulic pressure stabilizer controlled loading system or the four-channel electro-hydraulic servo controlled loading system. Three channels of oil are output and divided into six channels by the flow divider 22 to provide oil for the six flat jacks in three orthogonal directions around the test block 58. The flow divider 22 is shown as FIG. 10.

One oil channel is divided into two channels by the flow divider 22 and three channels are divided into six channels in total to ensure that stresses loaded by two flat jacks in opposite direction are equal. The oil pipes and the flow divider 22 are connected by quick connectors 53 for easy connection and disconnection. After the experiment, oil pipes of six flat jacks are removed from the flow divider 22.

Furthermore, three oil inlet pipes 47 are mounted on one side of the flow divider 22 and six oil outlet pipes 48 are installed on the other side of the flow divider 22. Each oil inlet pipe 47 is connected with two oil outlet pipes 48. The flow divider 22 is seated in the flow divider casing 50. The flow divider casing 50 includes three oil inlet holes on one side, six oil outlet holes on the other side, an upper cover 49 and an oil drain valve 51 at the bottom.

The flow divider 22 includes three oil inlet pipes 47 on one side and six oil outlet pipes 48 on the other side. The oil pressure of three oil inlet pipes 47 is provided by the loading system 26. One oil channel is divided into two channels in the flow divider 22 and six oil channels are output at last. Each oil inlet is communicated with two oil outlets by a three-way connection to ensure that the oil pressures of two outlet pipes are equal and the stresses loaded by two oil channels in one principal direction are equal. The oil pipes and the flow divider 22 are connected by quick connectors 53 for easy connection and disconnection. Three pressure sensors 20 are mounted at the entrance of the three oil inlets to monitor the pressure of each oil channel.

However, each time after the experiment when the oil pipes are removed from the flow divider 22, oil flows out of the oil pipe and pollutes the test site, which is wasteful and hard to clean up. The oil spilling is urgent to be eliminated.

Figure 11:
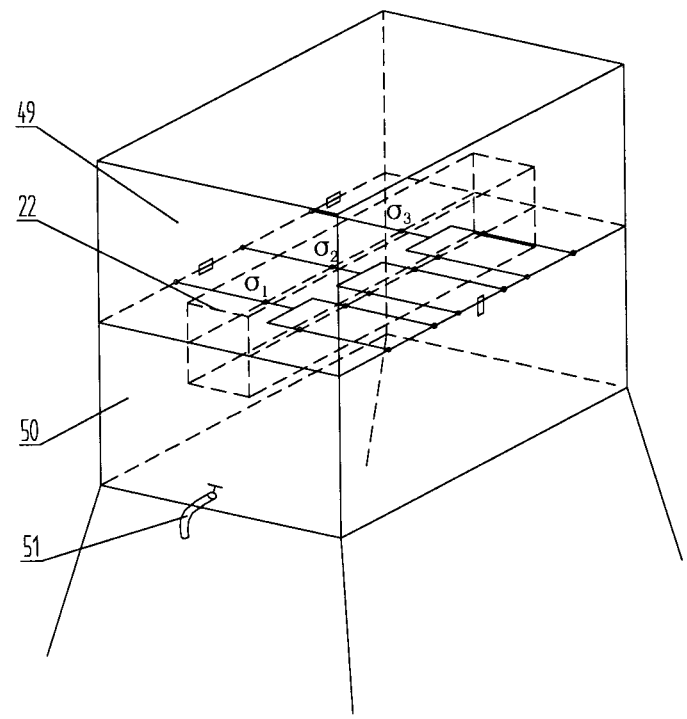
FIG. 11 shows a schematic diagram of installation structure of flow divider according to an embodiment of the present invention.

Based on the above analysis, a new flow divider device is designed. The flow divider 22 is seated in the flow divider casing 50 as shown in FIG. 11. Three holes are drilled through one side of the flow divider casing 50. Three oil pipes, which is loaded by the hydraulic control system or the electro-hydraulic servo control system, enter into the flow divider casing 50 through the three holes and are connected with the flow divider 22. Six holes are drilled through the other side of the flow divider casing 50 as export of six oil outlet pipes 48. The cover 49 can be opened for connection and disconnection of oil pipes. Three pressure sensors 20 are disposed at the entrance of oil inlet pipes 47 of the flow divider 22 to monitor the confining pressure. Three holes are drilled through the upper part of the flow divider casing 50 to allow the wires of the three pressure sensors 20 to pass through. An oil drain valve 51 is arranged at the bottom of the flow divider casing 50 to discharge the accumulated oil for cyclic utilization.

That is to say the flow divider casing 50 includes three holes on one side. Three oil pipes, which are loaded by the hydraulic control system or the electro-hydraulic servo control system, enter into the flow divider casing 50 through the three holes and are connected with the flow divider 22. Six holes are drilled through the other side of the flow divider casing 50 as export of six oil outlet pipes 48. The cover 49 can be opened for connection and disconnection of oil pipes. Three pressure sensors 20 are disposed at the entrance of oil inlet pipes 47 of the flow divider 22 to monitor the triaxial confining pressure. The flow divider casing 50 is provided with three openings at the upper part to allow the wires of three pressure sensors 20 to pass through. An oil drain valve 51 is arranged at the bottom of the flow divider casing 50 to discharge the accumulated oil for cyclic utilization.

The passages of oil pipes on the flow divider casing 50 are aligned with the oil pipe joints on the flow divider 22 to ensure that the oil pipes are straight in the flow divider casing 50 after the oil pipes are connected with the flow divider 22. A certain amount of space at the bottom of the flow divider casing 50 is reserved to store oil.

With the above device, the connection and disconnection of oil pipes are conducted in the flow divider casing 50. The leaked oil is gathered in the flow divider casing 50 and does not fall on the floor. The contamination is avoided and the gathered oil can be used circularly. The flow divider 22 is seated in the flow divider casing 50 which acts as an explosion protection. If accidental separation of the oil pipe from the flow divider 22 occurs due to abnormal oil pressure, the oil pipe and the high pressure oil can be isolated in the flow divider casing 50 to protect people from hurting.

The three pressure sensors are positioned close to the flat jacks to get accurate confining pressures.

To eliminate the leak of water and oil at the lower part of the true triaxial stress loading experimental frame 18, a large steel tray is placed under the true triaxial stress loading experimental frame 18 to collect leaked oil and water.

Furthermore, the monitoring system 8 includes a data processor, pressure sensors 20, and a deformation monitoring system. The pressure sensors and the deformation monitoring system are connected with the data processor by signal lines. Three pressure sensors 20 are mounted on the flow divider 22. The deformation monitoring system includes twenty-four displacement sensors 52. The displacement sensors 52 are installed in the arc-shaped subplates 41 of the flat jacks inconspicuously. Lines of displacement sensors 52 are placed in the grooves on the side surface of the arc-shaped subplates 41 and gathered to the upper surface of the arc-shaped subplates 41. The displacement sensors 52 are connected with data lines by quick connectors 53, the female connectors of which are set on the upper surface of the arc-shaped subplates 41.

The monitoring of deformation (rock and coal sample) has great significance for the determination of physical and mechanics parameters of samples and the analysis of fractures propagation. As a consequence, a deformation monitoring system 11 is added to the original monitoring system 8.

The function of the deformation monitoring system 11 is to monitor the strain of the test block 58 in three orthogonal directions during hydraulic fracturing experiment. The real-time monitoring function of the deformation monitoring system 11 is achieved by a data processor, namely a deformation monitoring computer 12. The loading of triaxial stresses on the test block 58 is conducted by five to six flat jacks. Therefore, the displacement sensors 52 are positioned on the flat jacks to monitor the deformation of the test block 58. Four displacement sensors 52 are installed on each flat jack to monitor the strain simultaneously and twenty displacement sensors 52 are installed totally.

The difficulties in installing the displacement sensors 52 are as flows. (1) Twenty displacement sensors 52 have a plurality of sensor lines. However, the original experimental system is compact with a plurality of component parts. The arrangement of sensor lines should not affect the original experiment system and be easy to be uninstalled. (2) To take out the test block 58 from the loading cavity, the experimental system must be disassembled each time after the experiment. So, the displacement sensors 52 must be easy to be connected and disconnected. (3) The displacement sensors 52 must be waterproof because leakage of water and oil often occur in the experiment.

Figure 12:
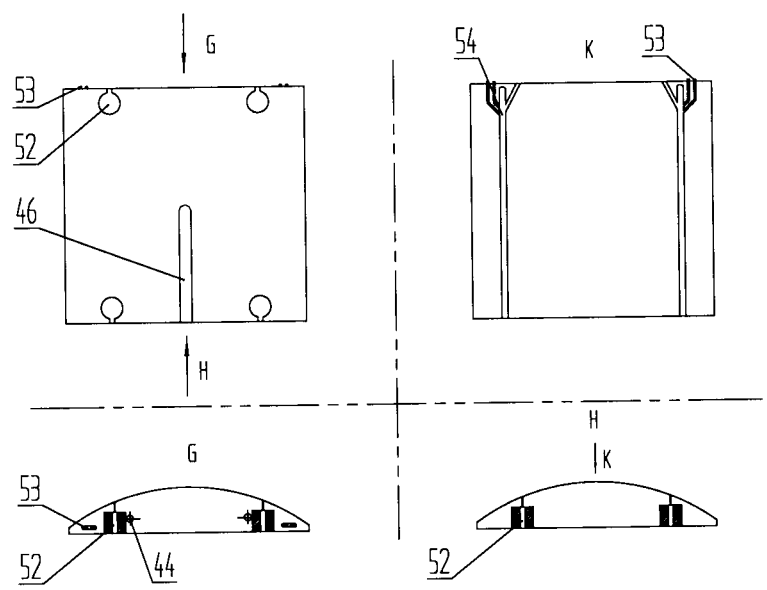
FIG. 12 shows a schematic diagram of arrangement of displacement sensors according to an embodiment of the present invention.
Figure 13:
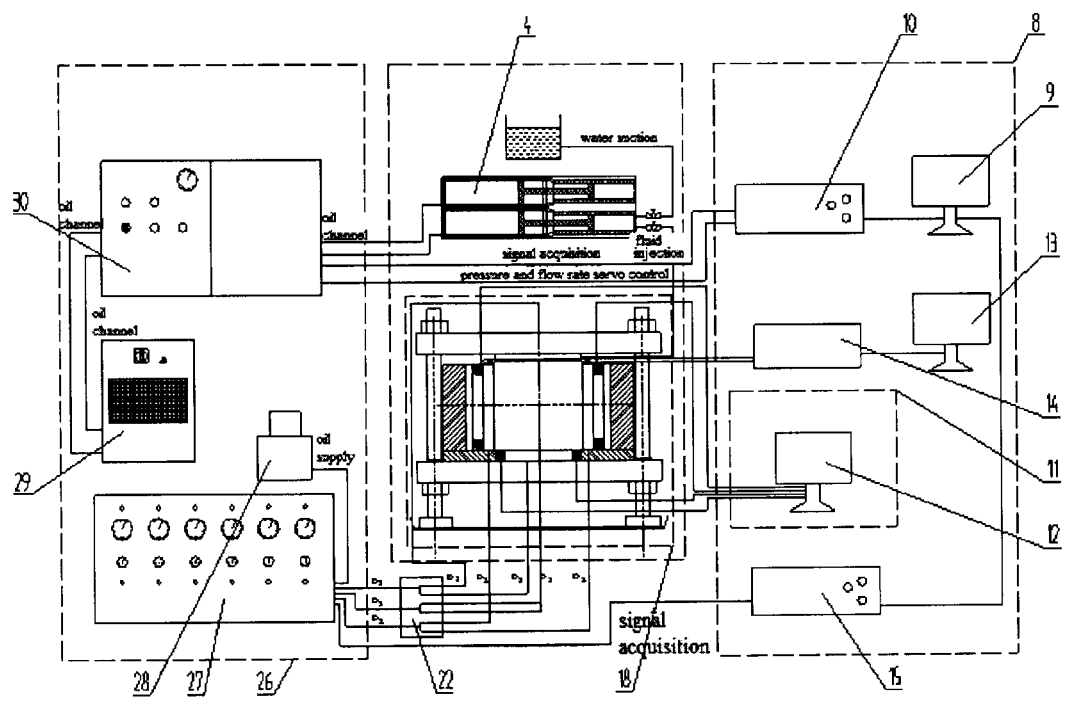
FIG. 13 shows a schematic diagram of the hydrofracturing experimental system under true triaxial stress according to an embodiment of the present invention.
Figure 14:
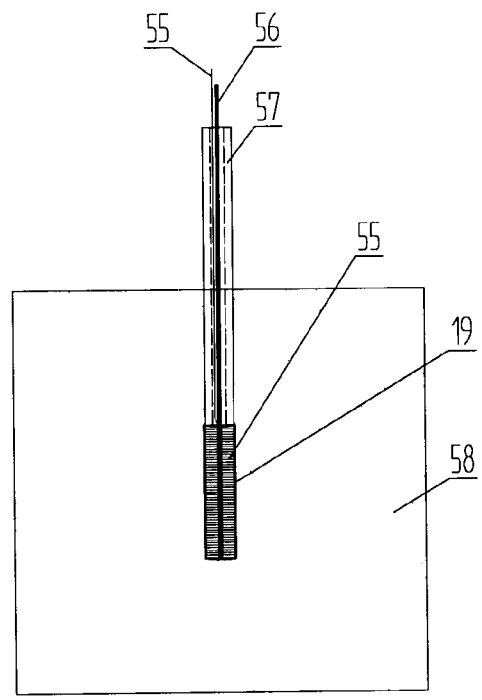
FIG. 14 shows a schematic diagram of stimulation method for naked borehole hydraulic fracturing according to an embodiment of the present invention.
Figure 15:
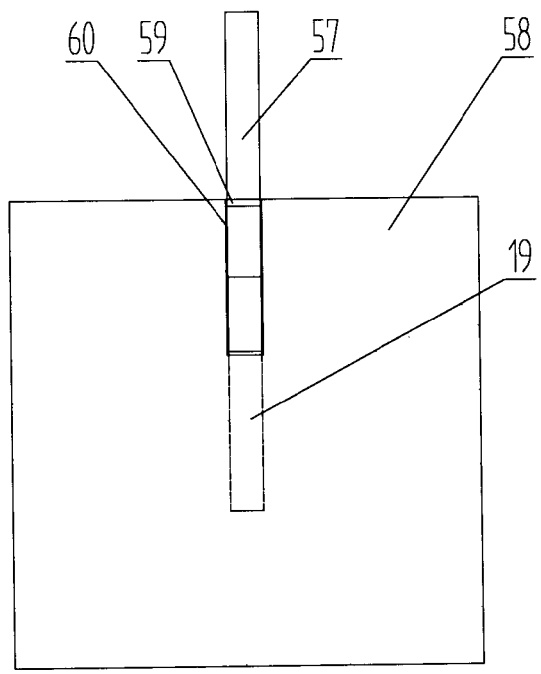
FIG. 15 shows a schematic diagram of sealing method for borehole in rock test block according to an embodiment of the present invention.
Figure 16:
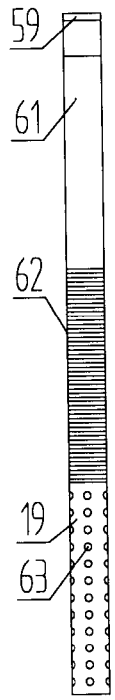
FIG. 16 shows a schematic diagram of structure of common borehole packer according to an embodiment of the present invention.
Figure 17:
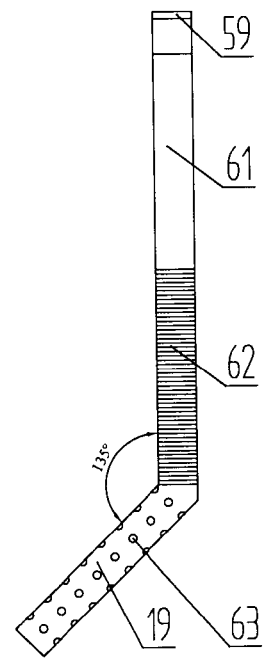
FIG. 17 shows a schematic diagram of structure of bending borehole packer according to an embodiment of the present invention.
Figure 18:
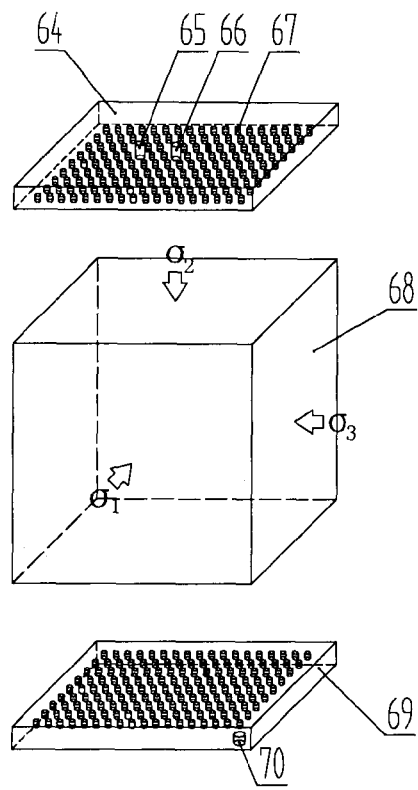
FIG. 18 shows a schematic diagram of stimulation of gas displacement according to an embodiment of the present invention.
Figure 19:
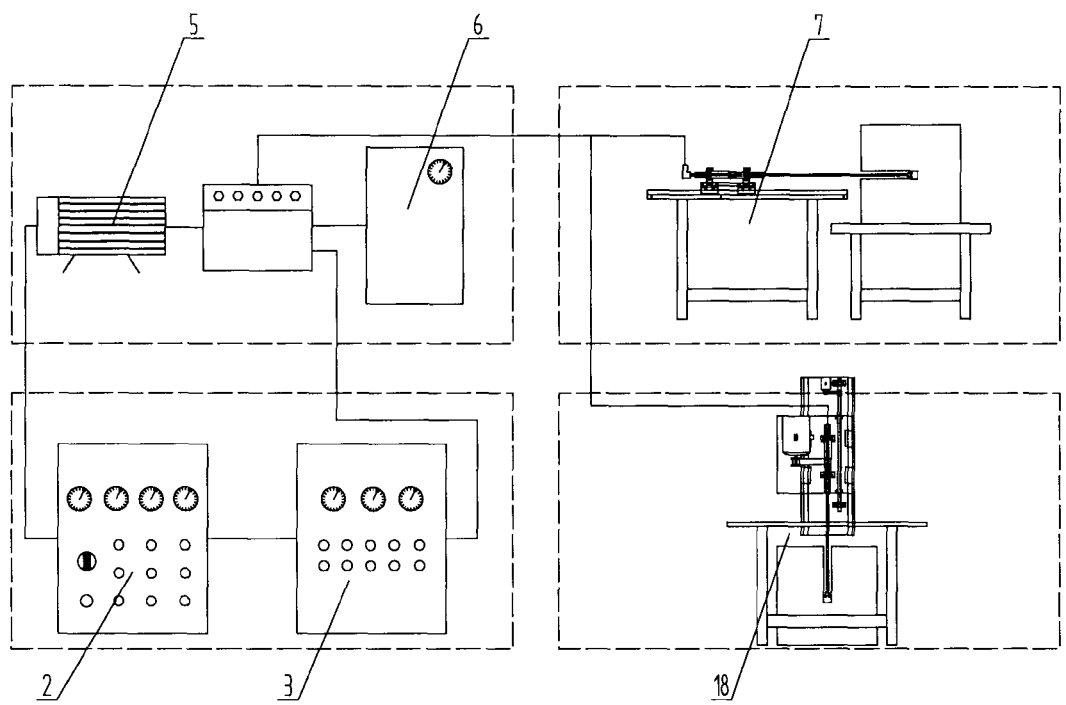
FIG. 19 shows a schematic diagram of structure of water jet slotting experimental system according to an embodiment of the present invention.

Based on the above considerations, the displacement sensors 52 are positioned inconspicuously in the arc-shaped subplates 41 to ensure that the displacement sensors 52 do not reach out of the arc-shaped subplates 41 when the flat jacks are being installed or the experiment is not started. Data lines of displacement sensors 52 in each arc-shaped subplates 41 are gathered to the upper surface of the arc-shaped subplates 41 where is convenient to connect the wires of the displacement sensor 52 and the data acquisition system. Quick connectors are installed on the upper surface of the arc-shaped subplates 41. The wires of data acquisition system and displacement sensor 52 are connected by quick connectors, which is convenient for the experimental frame 18 to be installed and uninstalled. The arrangement of displacement sensors 52 in each arc-shaped subplates 41 is shown as FIG. 12.

Two wire grooves 54 are cut on two sides of the curved surface of the arc-shaped subplates 41. The data lines of the displacement sensors 52 at the lower and upper part of the arc-shaped subplates 41 are gathered to the upper surface of the arc-shaped subplates 41 through the wire grooves 54 and connected with the female connectors of the quick connectors 53. The quick connector 53 is two to three mm higher than the surface of the arc-shaped subplates 41 to prevent water from entering into the connector. The male connectors of the quick connectors 53 are connected with data lines of the acquisition system. The wires of displacement sensors 52 are sealed in the wire grooves 54 of the arc-shaped subplates 41 to achieve the functions of fixing and water-proofing. The displacement sensors 52 and the quick connectors 53 are water proof. The resolution of displacement measurement can reach 0.001 mm. The effective range of the displacement sensor 52 is 0 to 25 mm. The displacement measurement system is reliable and accurate monitoring of strains of the test block 58 in three orthogonal directions can be achieved.

Signals collected by displacement sensors 52 are transferred to the data acquisition software by data lines. The displacement data can be displayed on the computer screen in real-time. The collected data can be recorded and stored in a plurality of forms such as diagram format and document format. The storage form is flexible and the sampling time and method can be set. The interval time at which the data is automatically saved can be set, and real-time storage of data can be realized (the data is not lost when power failure or shutdown of computer occurs). The original data cannot be changed. The collected data can be exported to TXT file or Access database file.

The innovations of the deformation monitoring system 11 are as follows. (1) The wires of the displacement sensors 52 are gathered to the upper surface of the arc-shaped subplates 41 by wire grooves 54 on the arc-shaped subplates 41. In this way, the functions of the original experimental system are not affected and the arrangement of multiple data lines is achieved. The experimental system is easy to be installed and uninstalled. (2) The data lines are connected with the quick connectors 53, which is easy to connect and disconnect. The female connector 53 is two to three millimeters higher than the upper surface of the arc-shaped subplates 41 to prevent water flowing into the connector. (3) The displacement sensors 52 are installed in the arc-shaped subplates 41 of the flat jack inconspicuously to ensure that the displacement sensors 52 stay within the subplates when the flat jacks are being installed or the experiment is not started.

The function of the displacement sensors 52 is to monitor the strains of the test block 58 in three orthogonal directions during the true triaxial stress loading process.

The position and installation of the twenty four displacement sensors 52 are as follows.

The displacement sensors 52 are installed in the arc-shaped subplates 41. Four displacement sensors 52 are installed in each arc-shaped subplates 41 to monitor the displacement simultaneously. The arrangement of the four displacement sensors 52 and their wires on each arc-shaped subplates 41 is shown as FIG. 12. The four displacement sensors 52 for the bottom surface of the test block 58 are positioned at the four corners of the bottom flat jack 38. The data lines come out of the true triaxial stress loading experimental system through the openings on the bottom subplates 37 and the baseplate 39.

In this invention, the wires of the displacement sensor 52 are gathered to the upper surface of the arc-shaped subplates 41 by wire grooves 54 on the arc-shaped subplates 41. In this way, the functions of the original experimental system are not affected and the arrangement of multiple data lines is achieved. The experimental system is easy to be installed and uninstalled. The data lines are connected by quick connectors 53, which is easy to connect and disconnect. The female connector of the quick connector 53 is two to three millimeters higher than the surface of the arc-shaped subplates 41 to prevent water flowing into the connector. The displacement sensors 52 are installed in the arc-shaped subplates 41 of the flat jacks inconspicuously to ensure that the displacement sensors 52 stay within the arc-shaped subplates when the flat jacks are being installed or the experiment is not started.

The monitoring system 8 includes the monitoring of the confining pressure of the test block 58, and the pressure and flow of water injection. The loading of confining pressure and water injection are controlled according to the feedback signals.

The implementation is as follows. The confining pressure signals are transferred to the hydraulic controller 15 of the six-channel hydraulic pressure stabilizer 27 by three pressure sensors 20, which are installed on the flow divider 22. Next, the signals are transferred to the monitoring computer 9, by which the loading of confining pressure is controlled according to the feedback signals. The pressure sensors 20 are installed on the high water pressure pipes, which are connected with the water cylinders of the four-channel oil-water transition supercharger 4. Four displacement sensors 52 are connected with the four pistons in the four-channel oil-water transition supercharger 4. Water pressure signals collected by pressure sensors 20 and signals of displacement sensors 52 are transferred to the servo controller 10, and then transferred to the monitoring computer 9, by which the water pressure and flow rate is controlled based on the feedback signals.

The monitoring system 8 includes the monitoring of AE and Microseismic events during the entire hydraulic fracturing experiment. PCI-2 eight-channel AE instrument 14 or Disp twenty four-channel AE instrument 14, RSM acoustic-waves-monitor and TDS-6 Microseismic event acquisition system are used to monitor the generation of micro-fracture and the propagation of fractures in real time.

Furthermore, the integrated experimental system of hydrofracturing, water jet slotting, seepage and gas displacement under true triaxial stress includes a water jet slotting experimental system. The water jet slotting system is connected with the true triaxial stress loading experimental frame 18 to conduct high pressure water jet slotting experiment.

Furthermore, the integrated experiment system of hydrofracturing, water jet slotting, seepage and gas displacement under true triaxial stress includes a hydrofracturing experimental system under true triaxial stress. The hydrofracturing system under true triaxial stress includes a similar simulation material casting system with naked borehole, a rock borehole sealing system, a bending borehole packer and an independent multi-borehole fracturing system. The similar simulation material casting system with naked borehole, the rock borehole sealing system, the bending borehole packer and the fracturing system are set in parallel. The similar simulation material casting system with naked borehole includes a thin round bar and a string wrapped on one end of the thin round bar. The rock borehole sealing system includes O-ring 59 and sealant 60. The bending borehole packer includes a vertical section without fracturing hole 63 and an inclined section with fracturing holes 63 to simulate hydraulic fracturing under heterotropic stress field. The independent multi-borehole fracturing system includes a set of molds with a cover plate of multi-borehole and a caging device. Hydrofracturing controlled by as many as five independent boreholes can be conducted.

The borehole of the test block 58 is sealed before the experiment.

To achieve good sealing effect, the borehole packer 57 is inserted into the similar material when the test block 58 is cast by similar simulation material. However, the naked borehole fracturing section 19 cannot be formed in this way. It is urgent to be solved that the naked borehole fracturing section 19 is formed when the borehole packer 57 is cast together with the test block 58 as well as good sealing effect is realized.

The central issue is how to form the naked borehole fracturing section 19 at the center of the test block 58 when preparing it. The implementation is as follows. A thin round rod 56 (for example thick iron wire) passes through the borehole packer 57 and reaches out of the bottom of the borehole packer 57 with length of the naked borehole length. Next, a string is wrapped on the rod from bottom to top layer by layer until the diameter of the rod wrapped with string is equal to the diameter of the borehole packer 57. At last, the string is passed through the borehole packer 57 and the borehole packer 57 is inserted into the similar material and cast with the test block 58 together. Two or three days later, the test block 58 is solidified and the molds can be dismantled. Before dismantling the molds, the thin round rod is pulled out of the borehole packer 57. Then the string is pulled out. The space occupied by the string 55 and the thin round rod 56 in the borehole forms the naked borehole fracturing section 19. The cubic test block 58 with the dimension of 300 mm×300 mm×300 mm is hereinafter taken as example to explain the method for forming the naked section of the borehole.

The length of the naked borehole fracturing section 19 is designed as 100 mm and the length and diameter of the borehole packer 57 are 220 mm and 18 mm respectively. When casting the test block 58, a thin round rod 56 is passed through the borehole packer 57 and reaches out of the bottom of the borehole packer 57 with length of 100 mm. Next, a cotton thread is wrapped on the rod from bottom to top layer by layer until the diameter of the rod wrapped with cotton thread reaches 100 mm, which is equal to the diameter of the borehole packer 57. And next, the cotton thread is passed through the borehole packer 57. And next, the borehole packer 57 together with the wrapped cotton string 55 is inserted into the similar simulation material. In the casting of the test block 58, the rod wrapped with string 55 is placed in the center of the test block 58. The borehole packer 57 is perpendicular to the upper surface of the test block 58 and the upper end of the borehole packer 57 is 120 mm higher than the upper surface of the test block 58. After the casting, the test block 58 is air dried for one to two days. The molds are dismantled when the test block 58 is solidified. The thin round rod 56 is first pulled out and next the cotton thread is pulled out. The space occupied by the cotton thread at the end of the borehole packer 57 forms the naked borehole fracturing section 19 with length of 100 mm in the test block 58.

The precautions are as follows. (1) The thin round rod 56 is as thick as possible, as long as its diameter is less than the inner diameter of the borehole packer 57. Thus, the diameter of the rod with one layer cotton thread can reach the external diameter of the borehole packer 57. The cotton thread is easy to be broken when pulled out of the borehole packer 57 if too many layers are wrapped on the rod. (2) The cotton thread is pulled out after the thin round rod 56, or the cotton thread is easy to be broken. (3) A layer of wet tissue or paper is wrapped on the string 55 to smooth the surface of the naked borehole fracturing section 19.

Naked borehole fracturing section 19 with random length and diameter can be simulated by the above method. The method is not limited by the length and diameter of the naked borehole fracturing section 19. The length and diameter of the naked borehole fracturing section 19 can be determined based on different requirements. This method has general applicability.

In hydraulic fracturing experiments for rock, the test block 58 is not need to be prepared by casting, so, the sealing method for rock is different from that of the similar simulating material. Before experiment, a borehole is drilled on the rock by drilling machine. Next, the borehole packer 57 is inserted into the borehole at certain depth to seal the borehole, and a naked borehole fracturing section 19 with certain length is reserved at the bottom of the borehole packer 57. However, the surface of the borehole drilled in rock is too smooth to be sealed. The sealing ability of sealant 60 cannot meet the requirements of the experiment. Experiments usually failed because high pressure water leaks from the interstice between the borehole packer 57 and the borehole surface.

Based on the above analysis, the borehole sealing method of combining the O-ring 59 with sealant 60 is used to seal the borehole. Several grooves are cut on the sealing section 61 of the borehole packer 57 and the O-rings 59 are mounted in the grooves. The sealant 60 is spread on the surface of the borehole packer 57 and then the borehole packer 57 is lowered into the borehole at designed depth. Cubic test block 58 with the dimension of 300 mm×300 mm×300 mm is hereinafter taken as example to explain the sealing method of combination of O-ring 59 and sealant 60.

The length of the borehole packer 57 is designed as 220 mm, and the length of the sealing section and the diameter of the borehole packer 57 are 100 mm and 25.8 mm respectively. Naked borehole fracturing section 19 with length of 100 mm is reserved at the bottom of the borehole packer 57. Three grooves are cut on the surface of the sealing section 61 of the borehole packer 57 with equal interval. Next, three O-rings 59 are mounted in the grooves and sealant 60 is spread on the outer surface of the borehole packer 57. And next, the borehole packer 57 is lowered into the borehole at depth of 100 mm to seal the borehole.

The borehole sealing method by combination of O-ring 59 and sealant 60 is not limited by the sealing length and the diameter of the fracturing hole 63. The sealing depth and borehole diameter can be determined based on experiment requirements. The number of O-rings 59 and the distance between O-rings 59 can also be changed. This sealing method has general applicability and good sealing effect, which meet the requirements of the experiment.

To meet different experiment requirements, different types of borehole packers 57 are designed. According to the angle between the naked borehole fracturing section 19 and the principal direction, the borehole packer 57 is divided into two categories: straight borehole packer (common borehole packer) and bending borehole packer.

The axial of borehole with common borehole packer is perpendicular to one of the principal stress directions to study the propagation law of hydraulic fractures that are perpendicular to the principal direction. According to different experiment requirements, common borehole packers with different size can be chosen. Borehole packer 57 with length of 320 mm, outer diameter of 20 mm and inner diameter of 10 mm is hereinafter taken as example to explain the inner structure of the borehole packer 57.

The length of the borehole packer 57 is 200 mm and the length of the fracturing section 19 is 100 mm. A part of the surface of the sealing section 61 with length of 100 mm is lathed with external thread, namely the thread section 62, to strengthen the bonding of the borehole packer 57 and the cement mortar, and improve the sealing effect. Four rows of fracturing holes 63 (12 fracturing holes in each row) with diameter of 4 mm are drilled through the fracturing section 19 to allow water to pass. To prevent the blocking of fracturing holes 63 by cement mortar when casting the test block 58, a layer of thin wet tissue is wrapped on the fracturing section 19 to simulate the naked borehole fracturing. The diameter of the borehole packer 57 and the length of the sealing section 61 and the fracturing section 19 can be changed based on specific experiment requirements.

Inclined boreholes are usually drilled in in-situ hydraulic fracturing. Most of the boreholes are not perpendicular to the principal direction. As a result, the study of propagation law of hydraulic fractures under oblique stress field is of great significance. Based on the above analysis, bending borehole packer 57 is designed to study the propagation law of hydraulic fractures under oblique stress field.

The bending borehole packer 57 with outer diameter of 20 mm and inner diameter of 10 mm as well as bending angle of 135 degrees is hereinafter taken as example to explain the inner structure of the bending borehole packer 57.

The bending borehole packer 57 includes a straight section without fracturing hole 63 and a bending section with fracturing holes 63. The length of the straight section is 220 mm while the length of the bending section is 90 mm. The angle between the straight section and the bending section is 135 degrees. The total length of the bending borehole packer is 310 mm. Four rows of fracturing holes 63 with diameter of 4 mm are drilled through the bending section to allow water to pass. A thin layer of wet tissue is wrapped on the fracturing section 19 of the borehole packer 57 to protect the fracturing holes 63 from being blocked by mortar cement, as well as to simulate the naked borehole fracturing. The sealing length is 200 mm. The part of the sealing section 61 with length of 100 mm and with screw thread on its surface is the thread section 62. The thread section 62 has the function of strengthening the bonding strength of the borehole packer 57 and the similar material and improving the sealing effect. In test block 58 with the size of 500 mm×500 mm×500 mm, the upper end of the borehole packer 57 is 20 mm higher than the upper surface of the test block 58. For test block 58 with the dimension of 300 mm×300 mm×300 mm, the upper end of the borehole packer 57 is 120 mm higher than the upper surface of the test block 58. Thus, the naked borehole fracturing section 19 of the bending section of the borehole packer 57 is placed at the center of the test block 58.

The angle between the straight section and the bending section of the borehole packer 57, the diameter of the borehole packer 57, the length of the sealing section 61 and the length of the naked borehole fracturing section 19 can be changed according to specific requirements of experiment.

Based on the requirements of multi-borehole hydraulic fracturing, a cover plate of the mold with multi-hole is designed. Multi-borehole hydraulic fracturing controlled by as many as five independent boreholes can be conducted. The test block 58 is cast using the mold with cover plate of multi-hole. The caging device 42 is used to ensure that the borehole packer 57 is placed at the center of the test block 58 and perpendicular to the upper surface of the test block

58. The caging device 42 is fixed on the cover plate by screw thread. The caging device 42 and the mold are used together to ensure that the fracturing hole 63 is accurately positioned and minimize the error of the experiment results as much as possible which is caused by movement of the fracturing hole 63.

Hydraulic fracturing is one of the most popular methods for in-situ stress measurement. It is the most effective way for deep area in-situ stress measurement. At present, hydraulic fracturing in rock for two-dimensional stress measurement is widely used. However, study of simulation of in-situ stress measurement by hydraulic fracturing in laboratory is insufficient. The simulation and verification of in-situ stress measurement by hydraulic fracturing can be conducted by this hydraulic fracturing experimental system under true triaxial stress.

The two-dimensional in-situ stress measurement refers to the measurement of two horizontal principal stresses which are perpendicular to the borehole axial. As a result, the vertical stress is assumed as the maximum principal stress. After the triaxial confining pressures are set, the confining pressures are loaded and the hydraulic fracturing is conducted. The water injection is stopped when the first fracturing occur. Then the water pressure decreases slowly. When the water pressure is steady, the water pressure is unloaded. Next, the water injection is restarted. When the hydraulic fractures reopen (drop in water pressure occurs), the water injection is stopped again and the water pressure is maintained stable. And next, the water pressure is unloaded again. The above process is repeated for several times. After the experiment, the first fracturing pressure, the reopen water pressure and the close pressure are read from the water pressure curve. The maximum, minimum and average horizontal principal stresses in each stage are calculated. The precision of the in-situ stress measurement is verified by comparing the pre-set value with the calculated average value.

In conventional hydraulic fracturing, the borehole axial is perpendicular to one of the principal stresses. However, in practical applications, the boreholes are mostly not perpendicular to the principal stress. The stress field obtained by hydraulic fracturing in borehole perpendicular to principal stress has great limitations.

Based on the above analysis, bending borehole packers 57 are used to study the propagation law of hydraulic fractures under oblique stress field and the distribution of stress. The bending angle of the naked borehole fracturing section 19 of the borehole packer 57 can be changed arbitrarily according to experiment requirements. The propagation law of hydraulic fractures under oblique stress field can be studied and the magnitude of the stress can be analyzed. The verification of in-situ stress measurement can be realized.

The test block 58 is cast by similar material in molds. Three sets of molds with the size of 300 mm×300 mm×300 mm and another three sets of molds with the size of 500 mm×500 mm×500 mm have been made. Three test blocks with the size of 300 mm×300 mm×300 mm and three test blocks with the size of 500 mm×500 mm×500 mm can be prepared for one time.

The above functions can be used in any combination based on different requirements. The water jet slotting, hydraulic fracturing and seepage functions can be used in any combination. For example, the effect of pore pressure on the breakdown pressure or on the propagation pressure can be studied by conducting hydraulic fracturing after the seepage experiment. The permeability change caused by hydraulic fracturing can also be investigated by conducting seepage experiment after hydraulic fracturing. The functions of gas displacement and hydraulic fracturing can also be used in combination. For example, the gas displacement effect by hydraulic fracturing can be studied by conducting hydraulic fracturing after the gas displacement experiment. The hydraulic fracturing and water jet slotting can be used cooperatively, the orientation effect of water jet slotting on the initiation and propagation of hydraulic fractures can be revealed by conducting hydraulic fracturing after water jet slotting experiment. The water jet slotting can be used together with the seepage experimental system. By measuring the seepage parameters of the coal block before and after water jet slotting under true triaxial stresses, the effect of water jet slotting on the seepage of coal can be studied.

Furthermore, the integrated experimental system of hydrofracturing, water jet slotting, seepage and gas displacement under true triaxial stress includes a seepage and gas displacement experimental system under true triaxial stress. The seepage and gas displacement experimental system under true triaxial stress includes an upper seepage plate 64 and a bottom seepage plate 69. Seepage orifices 67 are drilled orderly on the upper seepage 64 and the bottom seepage 69. Water inlet 65 and fracturing orifice 66 are also arranged on the upper seepage plate 64. Water outlet 70 is positioned on the bottom seepage plate 69.

The sealing of the test block 58 is the most difficult problem to be solved in seepage experiment. Both the sealing effect and the cost are taken into consideration. In the seepage experiment, seepage plates are placed above and bellow the test block 58. The four side surfaces of the test block 58 and four sides of the contact surfaces of the test block 58 and seepage plates are sealed by sealant 60. The sealant 60 has good viscosity. The coal sample 68 and seepage plates are bonded together by sealant 60 and become a whole structure. Meanwhile, the sealant 60 has good flexibility to bear deformation when the confining pressure is loaded. The coal sample 68 is hereinafter taken as example to explain the seepage and gas driving system.

The simulation experimental system of gas displacement is designed to realize the simulation of gas displacement in large size (400 mm×400 mm×400 mm) coal sample 68 under true triaxial stresses. Based on the MTS seepage experimental system, two seepage plates are made and placed above and below the coal sample 68 in this gas displacement simulation experimental system. The section size of seepage plates is the same as that of the coal sample 68 (400 mm×400 mm). Orifices with diameter of 2 mm are densely distributed on the seepage plates with row and column spacing of 10 mm×10 mm.

A coal sample or briquette coal with the dimension of 400 mm×400 mm×400 mm is placed between the upper and bottom seepage plates (400 mm×400 mm×50 mm) to form a combination structure with the dimension of 400 mm×400 mm×500 mm. Sealant 60 is spread on the four side surfaces of the combination structure with thickness of 50 mm to form a seepage unit with the size of 500 mm×500 mm×500 mm. High pressure water and gas inlet is positioned on the upper seepage plate 64 and fracturing orifice 66 is drilled through the center of the bottom surface of the upper seepage plate 64. When the seepage experiment is conducted, the fracturing orifice 66 is closed.

The hydraulic fracturing can be conducted through the fracturing orifice 66 on the upper seepage 64 after the seepage experiment of the coal sample 68. The fracturing orifice 66 is sealed when simulating gas displacement. In-situ coal sample 68 can be simulated by injecting gas into the coal sample 68 through the high pressure water and gas inlet on the upper seepage plate 64. Next, high pressure water is injected into the coal sample 68 to simulate gas displacement. The water (gas) inlet is connected with a three-way connector. One channel of the three-way connector is connected with the pressure sensor 20, the second flow sensor 21, the pressure regulating valve 23 as well as the gas storage tank 24 while another channel is connected with a valve and the four-channel oil-water transition supercharger 4.

Seepage orifices 67 are also distributed on the surface of the bottom seepage plate 69. A gas outlet is reserved on the bottom surface of the bottom seepage plate 69 and is connected with a rubber hose, valves and a flow sensor. In the experiment, gas is first injected into the coal sample 68 through the gas inlet on the upper seepage plate 64. When gas flows out of the gas outlet on the bottom seepage plate 69 steadily, the outlet valve is closed. The gas injection pressure is maintained for 24 hours, then the gas inlet valve is closed and the high pressure valve is opened to inject water into the upper seepage plate 64.

The seepage pressure in the seepage experiment under true triaxial stress is less than the confining pressure. The maximum confining pressure can reach to more than 20 MPa, so, the seepage pressure can reach to 14 to 15 MPa. However, there is no precedent of seepage experiment under true triaxial stress with seepage pressure reaching 14 to 15 MPa in China at present. Whether the seepage pressure can reach 14 to 15 MPa depends on the sealing effect. It can be realized theoretically by continuous tries and improvement in sealing ability. The coal sample seepage experiment with the dimension of 400 mm×400 mm×400 mm can be realized. Meanwhile, seepage experiment of rock can also be achieved. The sample size is determined based on specific experiment requirements.

The integrated true triaxial stress loading experimental system 25 includes pressure sensors 20, a second flow rate sensor 21, a pressure regulating valve 23, a gas storage tank 24, a four-channel oil-water transition supercharger 4, a true triaxial experiment frame 18, a concentration sensor 16, a first flow rate sensor 17 and an oil measure device 71.

Furthermore, the water jet slotting experimental system includes an electromechanical control cabinet 2, a high pressure pump control cabinet 3, a high pressure pump 5 and a water jet slotting device.

The water jet slotting device includes a rotary motor, a traction motor, a baseplate, two guide rails, a drill pipe, two axial bearings, a propulsion thread rod, a high pressure rotating joint, two sliding blocks and a support frame. The guide rails are fixed on the support frame and connected with the baseplate by two sliding blocks. The drill pipe is fixed on the base plate by two axial bearings. Two belt pulleys are fitted on the end of the rotary motor and the drill pipe. The drill pipe is driven to rotate clockwise or anticlockwise by the rotary motor through belt pulleys. The traction motor is mounted on the guide rails. The propulsion thread rod is fixed on the guide rails by two axial bearings at two ends of the propulsion thread rod. Screw threads exist on the surface of the propulsion thread rod. A belt pulley is fitted on one end of the propulsion thread rod and is connected with the belt pulley on the motor by a belt.

The water jet slotting experimental bench 7 includes a baseplate and a support frame. The rotary motor, the traction motor, the guide rails, the drill pipe, the axial bearings, the propulsion thread rod, the high pressure rotary and the sliding blocks are all mounted on the hydraulic cutting experiment bench 7.

When the traction motor is stopped and the rotary motor is started, the position of the baseplate is adjusted to insert the drill bit into the borehole at certain depth. Then the baseplate is fixed to fix the drill pipe in the vertical direction. The drill pipe is driven to rotate about its axis by the rotary motor and a radial slot with certain depth is slotted on the surface of the borehole in the standard test block 58. When the rotary motor is stopped and the traction motor is started, a high pressure water outlet of the drill pipe is fixed in one direction. The drill pipe is driven to move up and down together with the baseplate by the traction motor. Two axial slots with certain depth are slotted on the surface of the borehole of the standard test block 58 in certain direction. The water pressure and the slotting time are set based on experiment requirements to cut slot with certain depth.

There are two water jet slotting methods. In the first way, the support frame of the water jet slotting system 1 is set on flat floor and the guide rails are rotated by 90 degrees to be fixed vertically. The standard test block 58 is placed under the support frame of the water jet slotting system and the drill pipe is lowered into the borehole to cut a slot. In the second way, the standard test block 58 is placed on a special shelf with the borehole toward the water jet slotting device. The borehole is aligned with the drill pipe and then water jet slotting is conducted.

The integrated drilling and slotting drill bit of anchor cable drilling machine with small diameter ($\varphi$=32 mm or $\varphi$=28 mm) is used in water jet slotting to achieve the integrated functions of drilling and slotting.

Figure 9:
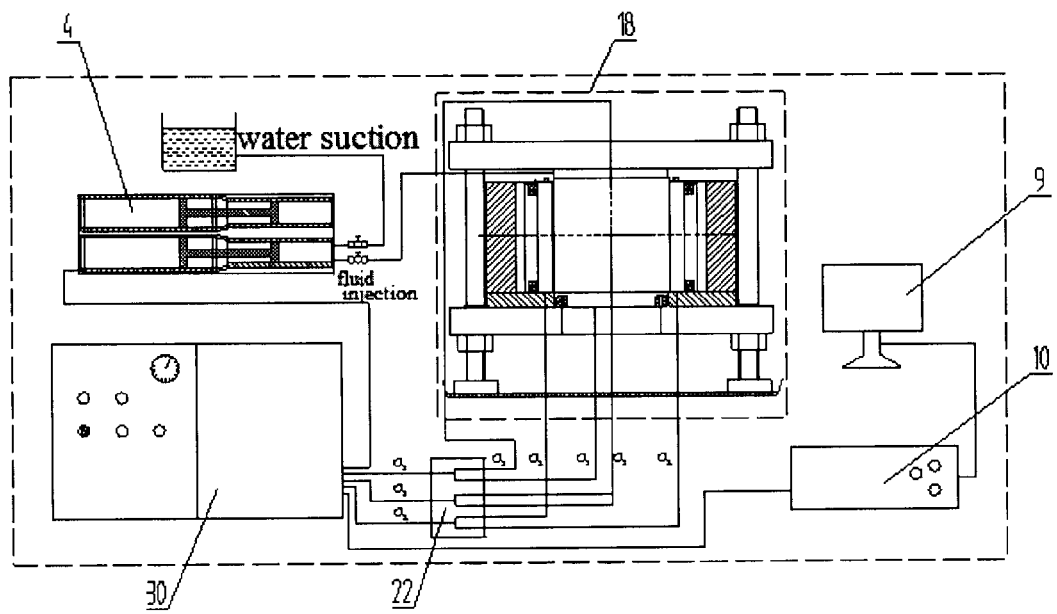
FIG. 9 shows a schematic diagram of the connection structure of four-channel electro-hydraulic servo controlled loading system and the true triaxial experiment frame according to an embodiment of the present invention.

Four lifting holes 44 are drilled on the upper cover plate 32 of the hydraulic fracturing experimental system to mount the lifting bolts, by which the upper cover plate 32 can be lifted by travelling crane. The four legs of the baseplate of the water jet slotting device is welded by angle iron. Four orifices with the same diameter of the lifting holes 44 are drilled through the end of the four legs of the baseplate. The legs of the baseplate are fixed on the upper cover plate 32 by bolts, the orifices of the legs and the lifting holes 44. Thus, the water jet slotting device cannot move during water jet slotting experiment and the quality of the slot is ensured. The above structure is shown as FIG. 9.

In the water jet slotting experimental system under true triaxial stress, the true triaxial confining pressure is loaded on the test block 58 by the hydraulic fracturing experimental bench under true triaxial stress, the water jet slotting device is fixed on the hydraulic fracturing experimental bench to cut a slot on the surface of the borehole in the test block 58. Axial slot and radial slot can be cut by the water jet slotting device. Water jet slotting with coal and rock mass under in-situ stress can be simulated. After water jet slotting, the test block 58 is sealed to study hydraulic fracturing after water jet slotting. The water jet slotting experimental system mainly includes two parts, the water jet slotting device and the true triaxial stress loading device.

The water jet slotting device includes a traction motor, a rotary motor, two sliding blocks, two guide rails, a support frame, a drill pipe and a drill bit, and the like. The rotary motor and the drill pipe are driven to move along the guide rails by the traction motor. The drill bit, therefore, is driven to move up and down in the borehole of the test block 58 and an axial slot is cut on the surface of the borehole. The rotary motor is fixed on the sliding blocks and connected with the drill pipe. The drill pipe and the drill bit are drive to rotate by the rotary motor in the borehole of the test block 58 to cut a radial slot on the surface of the borehole.

The fixing of the water jet slotting device and the true triaxial stress loading frame is the key factor for successful water jet slotting. Because the water jet slotting device is heavy, lifting bolts are mounted on the water jet slotting device to lift the device by travelling crane. After the water jet slotting device is lifted on the true triaxial loading frame, a caging device is installed through the opening at the center of the upper cover plate 32 to limit the movement of the drill pipe. Next, the legs of the baseplate of the water jet slotting device is fixed on the upper plate 32 by bolts to limit the movement of the water jet slotting device and ensure the quality of the slot.

After the water jet slotting experiment, the water jet slotting device and the caging device 42 are lowered on the floor. The seepage experiment system can be installed to conduct the seepage experiment after water jet slotting. Or sealing the borehole with special borehole packer 57 to conduct hydraulic fracturing of the test block 58 after water jet slotting. The borehole observation instrument can also be inserted into the borehole to observe the fracture propagation. Different functions can be realized according to different requirements.

Preparing Work Before the Experiment

1. The preparation of test block 58. The test block 58 is prepared a month before the experiment. When preparing the test block 58, the mold is assembled first and the similar simulation material (the test block 58 is usually made of cement mortar, the mass ratio of fine sand:cement:water is 3.5:1:0.3) is prepared. Next, the similar simulation material is poured into the mold and the borehole packer 57 is inserted into the similar simulation material. One to two days after the test block 58 is cast, the mold is dismantled. The test block 58 is maintained by water. After 28-days air-drying, the test block 58 can be used for experiment.

2. The placement of the test block 58 and the assembly of the experiment bench. The test block 58 is placed in the experiment frame by lifting device. Next, the four sides flat jacks, the arc-shaped subplates, the caging device 42, the upper water injection plate, the upper cover plate 32 are installed successively. And next, the eight pre-tighten nuts 34 are tighten. Thus the experiment bench is installed.

3. The connection of oil pipes and the installation of the AE monitoring system. The oil pipes 45 of the five flat jacks are connected with the flow divider 22. The liens of AE instrument are connected and the AE probes are placed on the surface of the flat jacks, which contact directly with the test block 58.

4. The water suction process and the loading of confining pressures. Turn on the six-channel hydraulic pressure stabilizer 27 and the four-channel servo loader 30. Automatic water suction of the water cylinder is conducted and controlled by the magnetic valve that is mounted on the water inlet pipe of the four-channel oil-water transition supercharger 4. The magnetic valve is controlled by the software of the monitoring computer 9. Red poster dye is added to water tank 6 to make it easier to observe the shape of hydraulic fractures after experiment. When the water suction is finished, the true triaxial confining pressures are loaded by the six-channel hydraulic pressure stabilizer 27, which is controlled by the monitoring computer 9. The confining pressure is kept stable for 5 min after it reaches the preset value.

5. Conducting hydraulic fracturing experiment according to the experiment scheme. When the confining pressures have been maintained for 5 min, the water injection mode is set (in the way of MPa/min, mL/min or pulse injection) by the software and high pressure water is injected into the test block 58 by the four-channel oil-water transition supercharger 4, which is controlled by the four-channel servo-control loader 30. Meanwhile, the AE signals are recorded by the mainframe of the AE instrument 14. The water injection is stopped when water drops from the bottom of the experiment bench, indicating that the test block 58 has failed. Then the experiment is stopped.

6. After the experiment, the recorded data is saved and the confining pressure is unloaded. The oil pipes connected with the flow divider 22 are disconnected and the AE probes are collected. The experiment bench is dismantled and the test block 58 is taken out of the experiment frame. Then the test block 58 is split along the main hydraulic fracture to observe the shape of hydraulic fractures. Photos or vides of the whole experiment are recorded.

The integrated experimental system of hydrofracturing, water jet slotting, seepage and gas displacement under true triaxial stress is provided by the present invention, by which, we conduct the seepage and fluid-structure interaction experiments with high seepage pressure under true triaxial stress, the mechanical deformation tests of coal and soft rock under true triaxial stress, and experiments of borehole drilling, water jet slotting and high pressure water. The present invention is equipped with the functions of hydrofracturing, seepage, gas displacement and water jet slotting. These functions can be used in any combination according to specific experimental requirements. The hydraulic fracturing process can be studied and judged systematically and precisely using the present invention, and the construction effect and safety are improved significantly.

It should be appreciated that the foregoing is only preferred embodiments of the invention and is not for use in limiting the invention. Although this invention is described in detail based on the foregoing preferred embodiments, it is apparent for those skilled in the art that modification of technical proposals or equivalent substitution of part or all of the technical features can be made. Any modification, equivalent substitution, and improvement without departing from the spirit and principle of this invention should be covered in the protection scope of the invention.

The invention claimed is:

1. An integrated experimental system of hydrofracturing, water jet slotting, seepage and gas displacement under true triaxial stress, comprising:
    a true triaxial stress loading experimental frame, a loading system and a monitoring system, wherein:
        the true triaxial stress loading experimental frame and the loading system are connected by oil pipes;
        the monitoring system is connected to the true triaxial stress loading experimental frame and the loading system by signal lines;
        the true triaxial stress loading experimental frame comprises a main experimental bench and six flat jacks;
        a loading cavity for a test block is equipped in the main experimental bench;
        the six flat jacks are set in the loading cavity; and
        a space of a regular hexahedron is formed by the six flat jacks.

2. The integrated experimental system of hydrofracturing, water jet slotting, seepage and gas displacement under true triaxial stress according to claim 1, wherein:
    the main experimental bench comprises a baseplate, an upper cover plate, displacement restricting steel columns, a caging device, an annulus steel ring and arc-shaped subplates;
    the upper cover plate and the baseplate are positioned at the two ends of the annulus steel ring;
    the upper cover plate and the baseplate are fitted together by the displacement restricting steel columns;

the number of the arc-shaped subplates is four, the arc-shaped subplates are arranged uniformly in the annulus steel ring; and the four arc-shaped subplates contact with the four side surfaces of the regular hexahedron.

3. The integrated experimental system of hydrofracturing, water jet slotting, seepage and gas displacement under true triaxial stress according to claim 2, wherein:

the loading system comprises a six-channel hydraulic-pressure stabilizer controlled loading system and a four-channel electro-hydraulic servo controlled loading system;

the six-channel hydraulic-pressure stabilizer controlled loading system and the four-channel electro-hydraulic servo controlled loading system are connected with the true triaxial stress loading experimental frame by oil pipes;

the four-channel electro-hydraulic servo controlled loading system is connected to the true triaxial stress loading experimental frame by a four-channel oil-water transition supercharger; and the six-channel hydraulic-pressure stabilizer controlled loading system is connected to the true triaxial stress loading experimental frame by a flow divider.

4. The integrated experimental system of hydrofracturing, water jet slotting, seepage and gas displacement under true triaxial stress according to claim 3, wherein:

the flow divider comprises three oil pipes on the inlet side and six oil pipes on the outlet side;

each oil inlet pipe is connected with two oil outlet pipes;

the flow divider is positioned in a flow divider case;

three oil inlet holes exist on one side of the flow divider case, and six oil outlet holes exist on the other side of the flow divider case;

the flow divider comprises an upper cover; and the flow divider comprises an oil draining valve at the bottom.

5. The integrated experimental system of hydrofracturing, water jet slotting, seepage and gas displacement under true triaxial stress according to claim 3, wherein:

the monitoring system comprises a data processor, pressure sensors and a deformation monitoring system;

the pressure sensors and deformation monitoring system are connected with the data processor by signal lines;

three pressure sensors are installed on the flow divider;

the deformation monitoring system comprises 24 displacement sensors;

the displacement sensors are mounted in the arc-shaped subplates of the flat jacks;

the lines of the displacement sensors are placed in grooves on the side surface of the arc-shaped subplates and gathered to the upper surface of the arc-shaped subplates; and the displacement sensors are connected with data lines by quick connectors, the female connectors of which are installed on the upper surface of the arc-shaped subplates.

6. The integrated experimental system of hydrofracturing, water jet slotting, seepage and gas displacement under true triaxial stress according to claim 1, further comprising a hydrofracturing system under true triaxial stress, wherein:

the hydrofracturing system under true triaxial stress comprises a similar simulation material casting system with naked borehole, a rock borehole sealing system, a bending hole packer and an independent multi-hole fracturing system;

the similar simulation material casting system, the rock borehole sealing system, the bending hole packer and the independent multi-hole fracturing system are set in parallel;

the similar simulation material casting system includes a round bar and a string wrapped on one end of the bar;

the rock borehole sealing system comprises O-rings and sealant;

the bending hole packer includes a vertical section without fracturing holes and an inclined section with fracturing holes, to simulate hydraulic fracturing under heterotropic stress field; and the independent multi-borehole fracturing system includes a set of molds with a cover plate of multi-borehole and a caging device, by which hydrofracturing controlled by as many as five independent boreholes can be conducted.

7. The integrated experimental system of hydrofracturing, water jet slotting, seepage and gas displacement under true triaxial stress according to claim 1, further comprising a seepage and gas displacement system under true triaxial stress, wherein:

the seepage and gas displacement system under true triaxial stress includes an upper seepage plate and a bottom seepage plate;

seepage orifices are arrayed on the upper and bottom seepage plates;

the upper seepage plate comprises a water inlet and a fracturing orifice;

the lower seepage comprises a water outlet; and the interstice between the seepage and gas displacement system under true triaxial stress and the test block is cast by sealant.

8. The integrated experimental system of hydrofracturing, water jet slotting, seepage and gas displacement under true triaxial stress according to claim 1, further comprising a water jet slotting system, wherein the water jet slotting system is connected with the true triaxial stress loading experimental frame to conduct water jet slotting experiments.

9. The integrated experimental system of hydrofracturing, water jet slotting, seepage and gas displacement under true triaxial stress according to claim 8, wherein:

the water jet slotting system comprises an electromechanical control cabinet, a high pressure pump control cabinet and a water jet slotting device;

the water jet slotting system comprises a rotary motor, a traction motor, a baseplate, two guide rails, a drill pipe, two axial bearings, a propulsion thread rod, a high pressure rotating joint, two sliding blocks and a support frame;

the guide rails are fixed on the support frame;

the baseplate is connected with the guide rails by two sliding blocks;

the drill pipe is fixed on the baseplate by the axial bearings;

two belt pulleys are fitted on the end of the rotating motor and the drill pipe;

the drill pipe is driven to rotate clockwise or anticlockwise by the rotating motor through belt pulleys;

the traction motor is fixed on the guide rails;

the propulsion thread rod is fixed on the guide rails by two axial bearings;

threads exist on the surface of the propulsion thread rod; and a belt pulley is fitted on one end of the propulsion thread rod and is connected with the belt pulley on the motor by a belt.

* * * * *